(12) United States Patent
Tanaka

(10) Patent No.: US 11,051,778 B2
(45) Date of Patent: Jul. 6, 2021

(54) X-RAY FLUOROSCOPIC IMAGING APPARATUS

(71) Applicant: Shimadzu Corporation, Kyoto (JP)

(72) Inventor: Fumiaki Tanaka, Kyoto (JP)

(73) Assignee: Shimadzu, Kyoto (JP)

( * ) Notice: Subject to any disclaimer, the term of this patent is extended or adjusted under 35 U.S.C. 154(b) by 10 days.

(21) Appl. No.: 16/808,802

(22) Filed: Mar. 4, 2020

(65) Prior Publication Data

US 2020/0323505 A1 Oct. 15, 2020

(30) Foreign Application Priority Data

Apr. 10, 2019 (JP) .............................. JP2019-075080

(51) Int. Cl.
*G06K 9/00* (2006.01)
*A61B 6/02* (2006.01)
*A61B 6/00* (2006.01)
*A61B 6/04* (2006.01)

(52) U.S. Cl.
CPC .............. *A61B 6/487* (2013.01); *A61B 6/025* (2013.01); *A61B 6/0487* (2020.08); *A61B 6/4441* (2013.01); *A61B 6/5205* (2013.01)

(58) Field of Classification Search
CPC .... G01N 23/04; G01N 23/043; G01N 23/046; G01N 2223/40; G01N 2223/401; G01N 2223/406; G01N 2223/408; G01N 2223/419; G01N 2223/42; G01N 2223/402; G01T 1/163; A61B 6/025; A61B 6/027; A61B 6/03; A61B 6/032; A61B 6/037; A61B 6/02
See application file for complete search history.

(56) References Cited

U.S. PATENT DOCUMENTS

2011/0188726 A1* 8/2011 Nathaniel .............. A61B 6/025
382/132

FOREIGN PATENT DOCUMENTS

JP 2008-017965 A 1/2008

* cited by examiner

*Primary Examiner* — Don K Wong
(74) *Attorney, Agent, or Firm* — Muir Patent Law, PLLC

(57) ABSTRACT

This X-ray fluoroscopic imaging apparatus is provided with an image processing unit that corrects magnification of a plurality of X-ray images based on first height information and generates a first long image by stitching the images together. The image processing unit is configured to generate a second long image in which the magnification of the plurality of X-ray images is corrected based on second height information upon acceptance of an input of second height information after generating the first long image.

7 Claims, 11 Drawing Sheets

X-RAY FLUOROSCOPIC IMAGING APPARATUS

CROSS-REFERENCE TO RELATED APPLICATIONS

The related application number JP2019-075080, entitled "X-ray fluoroscopic imaging apparatus", filed on Apr. 10, 2019, and invented by Fumiaki Tanaka, upon which this patent application is based is hereby incorporated by reference.

BACKGROUND OF THE INVENTION

Field of the Invention

The present invention relates to an X-ray fluoroscopic imaging apparatus, and more particularly, to an X-ray fluoroscopic imaging apparatus for generating a long image.

Description of the Background Art

Conventionally, there has been known an X-ray fluoroscopic imaging apparatus for generating a long image by irradiating a subject with X-rays and stitching captured X-ray images together. Such an X-ray fluoroscopic imaging apparatus is disclosed, for example, in Japanese Unexamined Patent Application Publication No. 2008-17965.

The X-ray fluoroscopic imaging device disclosed in the above-described Japanese Unexamined Patent Application Publication No. 2008-17965 includes an X-ray source for irradiating a subject with X-rays, a two-dimensional X-ray detector arranged opposite to the X-ray source, and a long image synthesizing unit. In the above-described Japanese Unexamined Patent Application Publication No. 2008-17965, the two-dimensional X-ray detector is moved in the body axis direction of the subject, and respective imaging data obtained at the respective imaging positions are synthesized to obtain a long image.

SUMMARY OF THE INVENTION

Although not disclosed in the above-described Japanese Unexamined Patent Application Publication No. 2008-17965, in general, when X-ray images for generating a long image are captured, the X-ray fluoroscopic imaging device performs imaging in a state in which the height from the top board to the imaging target portion of the subject is set in advance. However, in an imaging target portion such as a blood vessel, for example, since the height from the top board differs depending on the position at which the imaging is performed, when the imaging is performed in a state in which the height from the top board is set to be constant, an X-ray image in which the imaging target portion is enlarged or reduced more than the actual size is acquired. Therefore, there is a problem that the stitching accuracy of the long image deteriorates.

The present invention has been made to solve the above-mentioned problems, and an object of the present invention is to provide an X-ray fluoroscopic imaging apparatus capable of generating a long image with high stitching accuracy.

In order to achieve the above-described object, an X-ray fluoroscopic imaging device according to one aspect of the present invention includes:

a top board configured to place a subject thereon;

an imaging unit including an X-ray source configured to emit X-rays to an imaging target portion in the subject placed on the top board and a detection unit configured to detect X-rays emitted from the X-ray source and transmitted through the subject, the imaging unit being configured to capture a plurality of X-ray images of the subject while changing a relative position with respect to the top board; and an image processing unit configured to generate a first long image by correcting a magnification of the plurality of X-ray images based on first height information and stitching them together, wherein the image processing unit is configured to generate a second long image in which the magnification of the plurality of X-ray images is corrected based on second height information upon acceptance of an input of the second height information after generating the first long image.

According to the present invention, the imaging unit configured to capture a plurality of X-ray images of the subject while changing a relative position with respect to the top board and an image processing unit configured to generate a first long image by correcting a magnification of the plurality of X-ray images based on first height information and stitching them together are provided, and the image processing unit is configured to generate a second long image in which the magnification of the plurality of X-ray images is corrected based on second height information upon acceptance of an input on the second height information after generating the first long image. With this, the size of the X-ray image can be adjusted by changing the magnification of the X-ray image by the second height information after generating the first long image using the first height information. Therefore, it is possible to provide an X-ray fluoroscopic imaging apparatus capable of generating a long image with high stitching accuracy.

Figure 2:
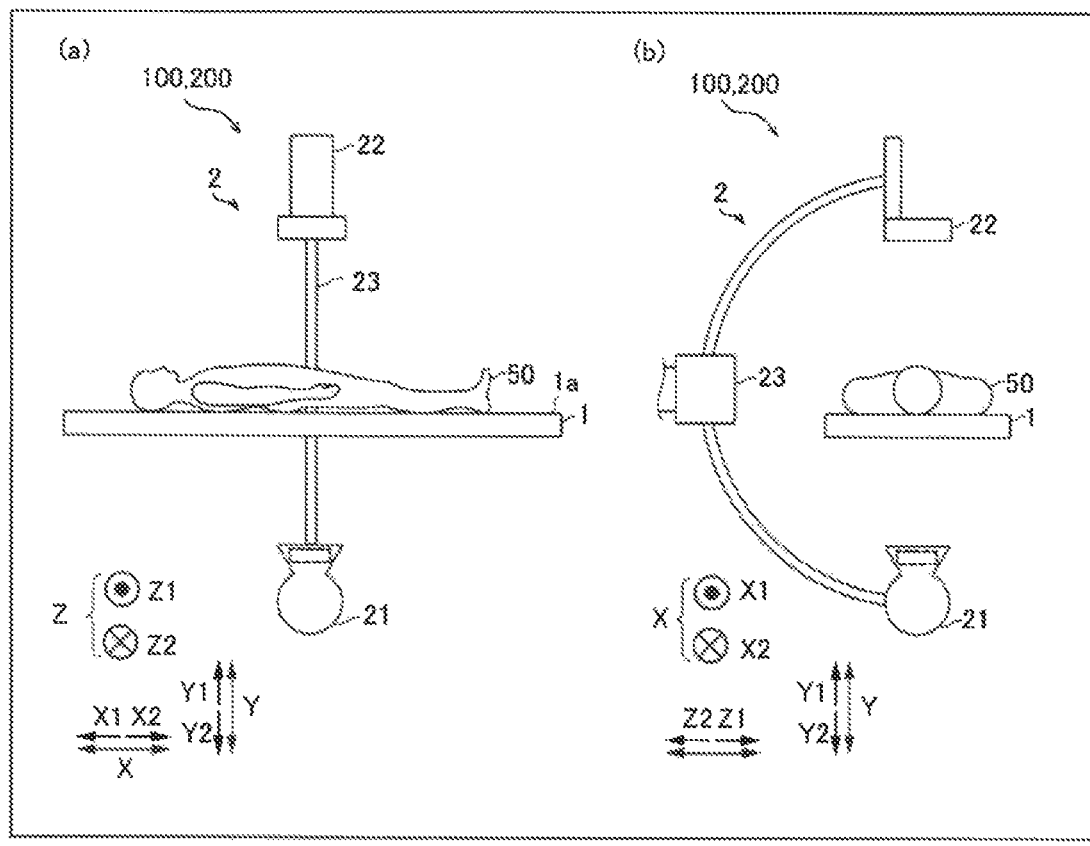

(a) of FIG. 2 is a side view showing the entire configuration of the X-ray fluoroscopic imaging apparatus.

(b) of FIG. 2 is a front view showing the entire configuration of the X-ray fluoroscopic imaging apparatus.

Figure 3:
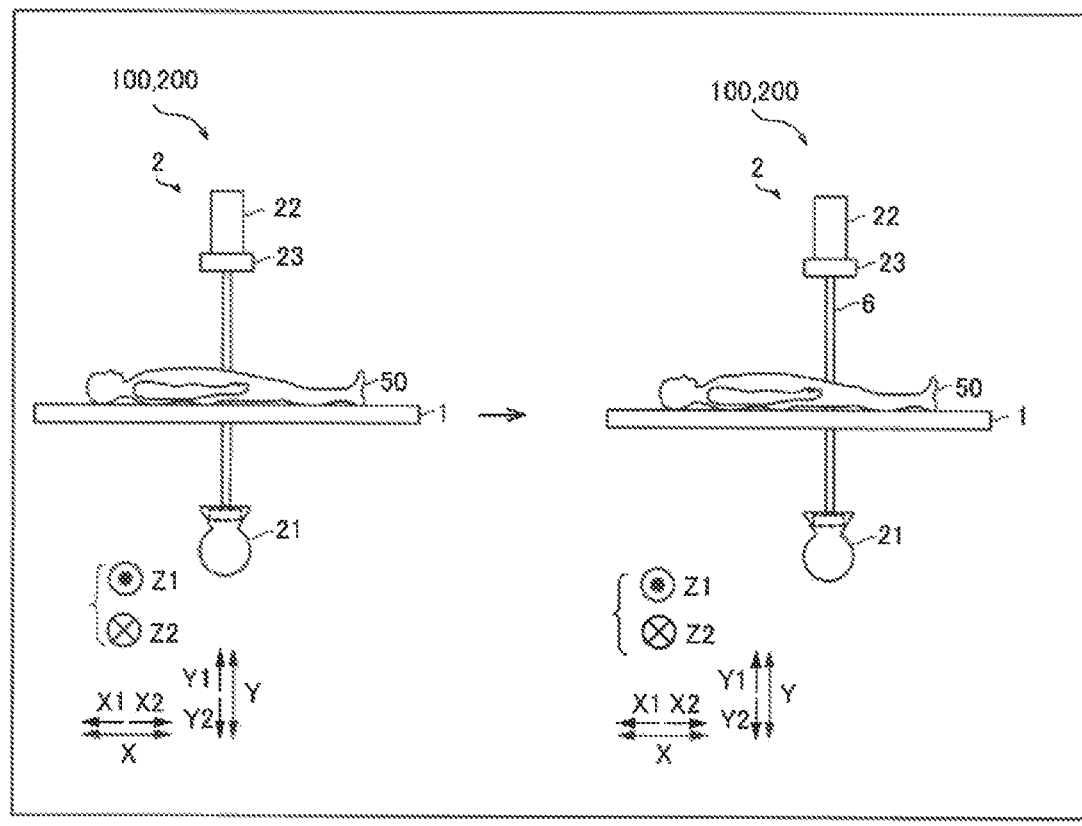

FIG. 3 is a diagram for explaining the top board moving image capturing.

Figure 4:
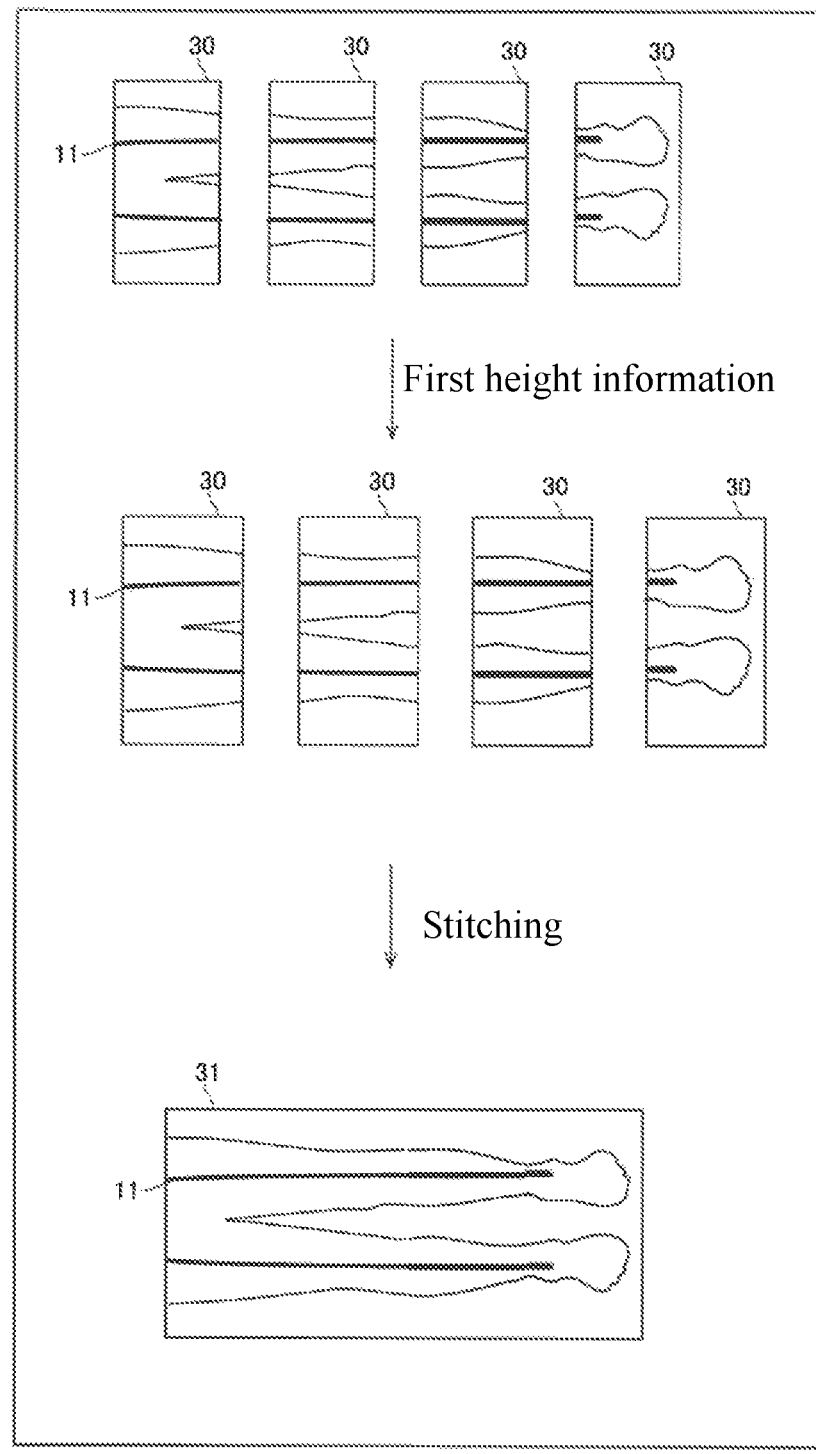

FIG. 4 is a diagram for explaining a long image generated based on first height information.

Figure 5:
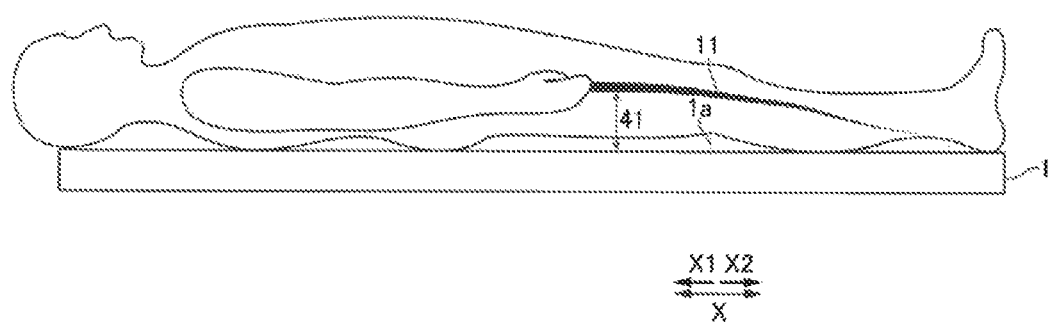

FIG. 5 is a diagram for explaining first height information.

Figure 6:
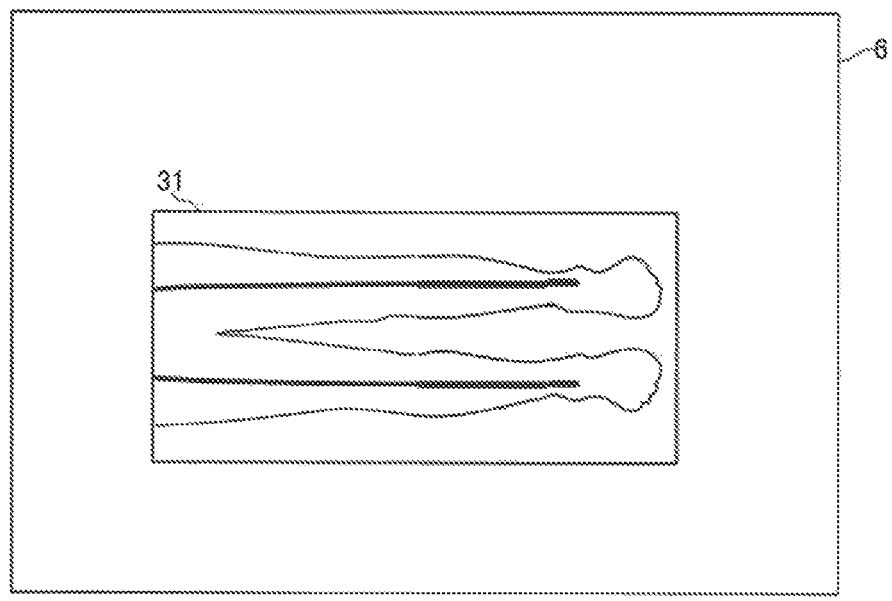

FIG. 6 is a diagram showing an example of a drawing displayed on a display unit.

Figure 7:
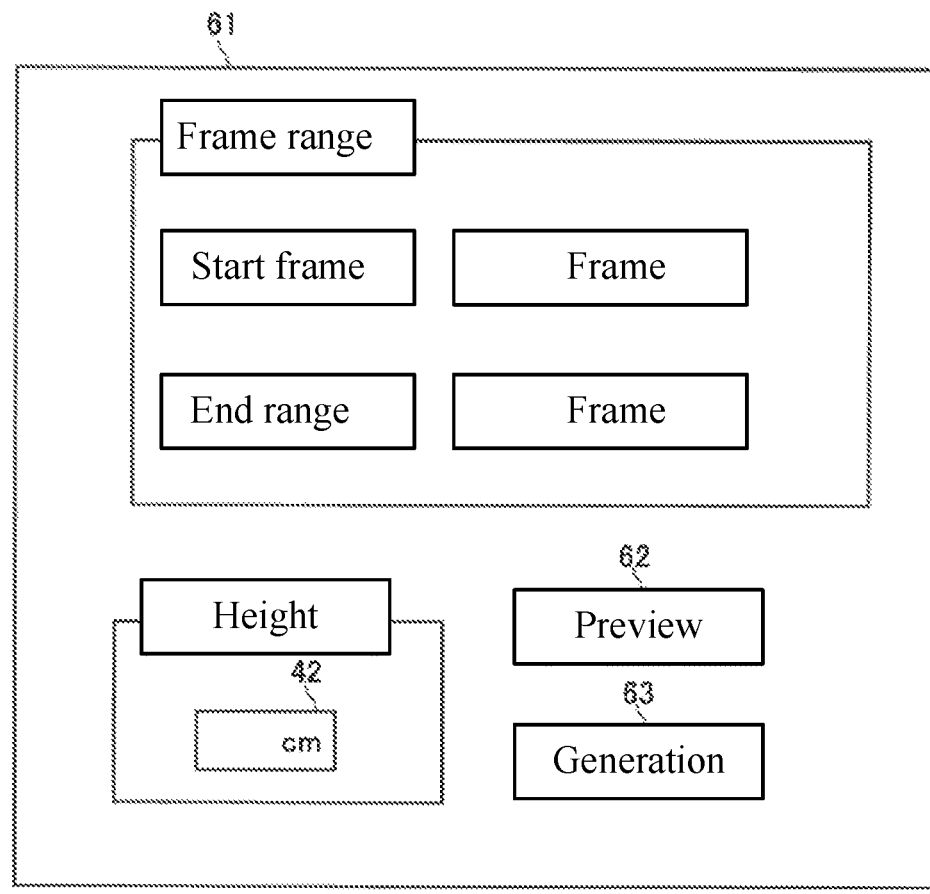

FIG. 7 is a schematic diagram showing a menu screen displayed on the display unit.

Figure 8:
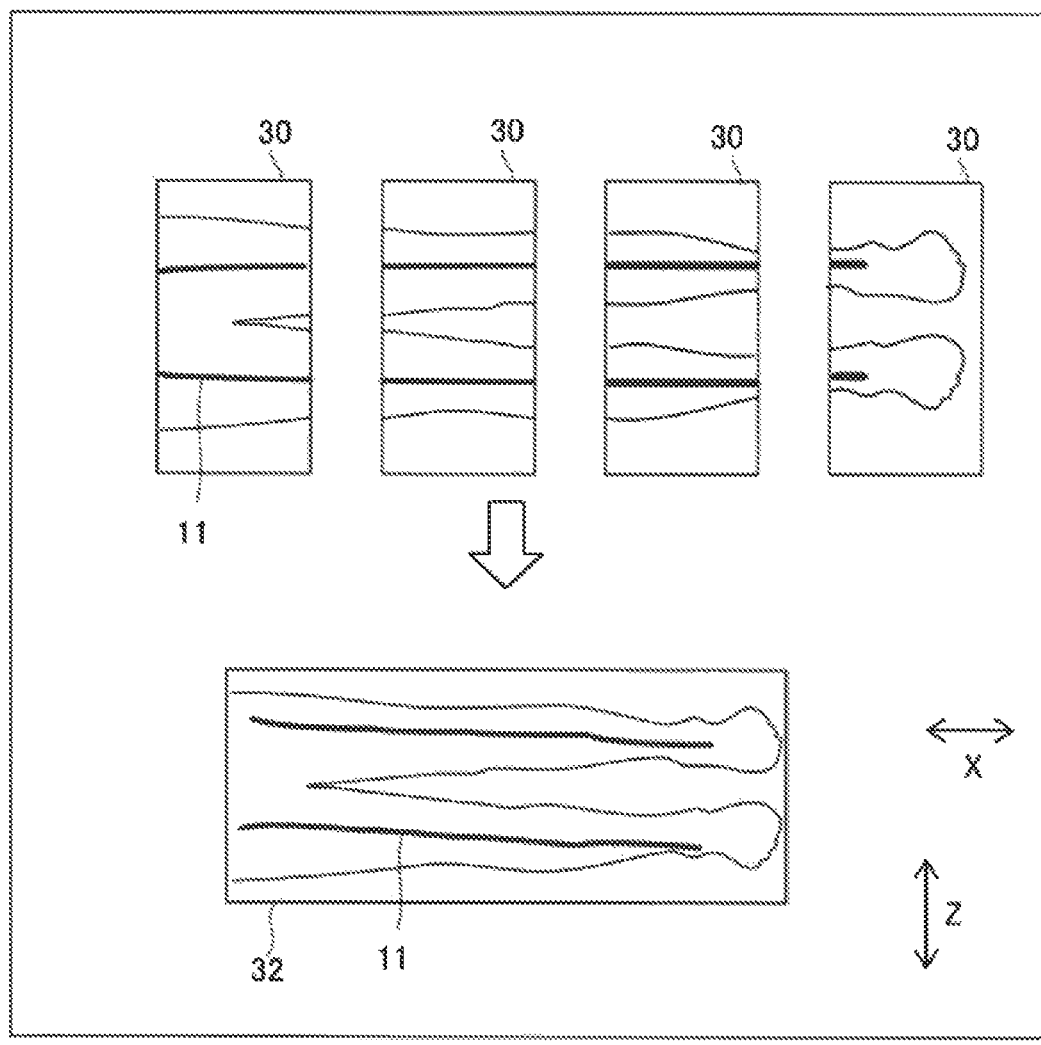

FIG. 8 is a diagram showing an X-ray image corrected by second height information.

Figure 9:
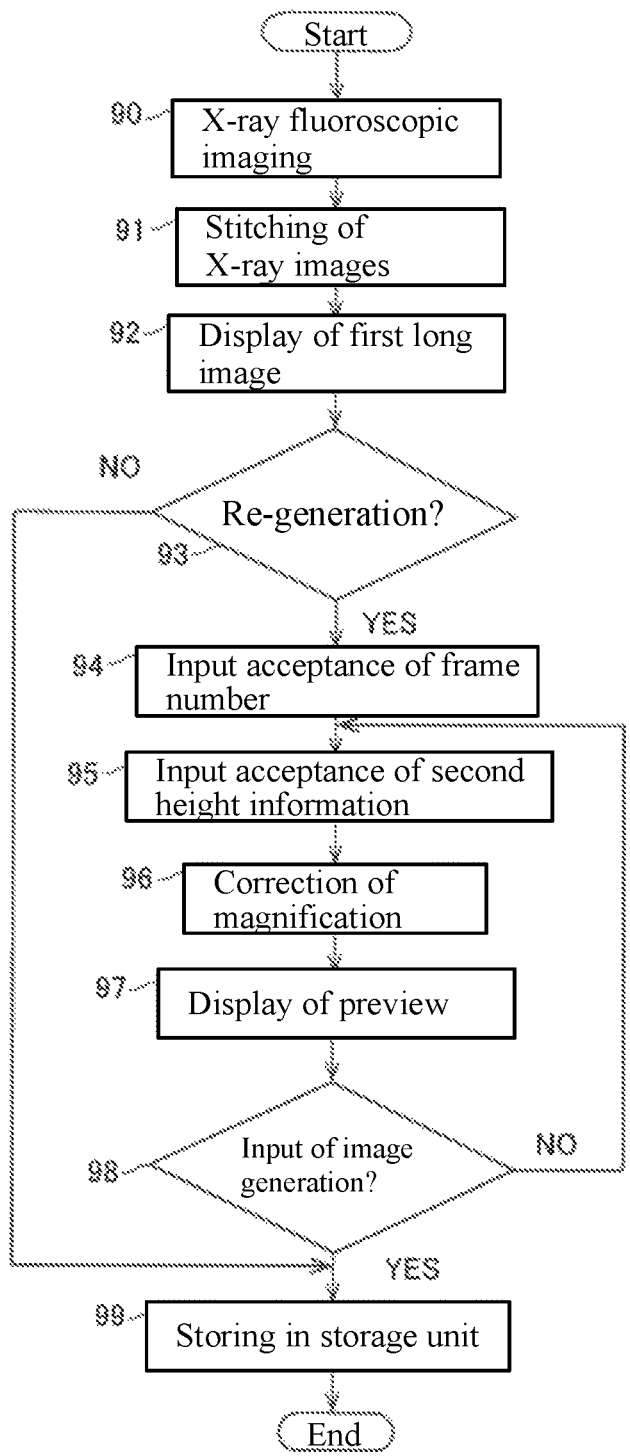

FIG. 9 is a flowchart showing a generation method of a long image.

Figure 10:
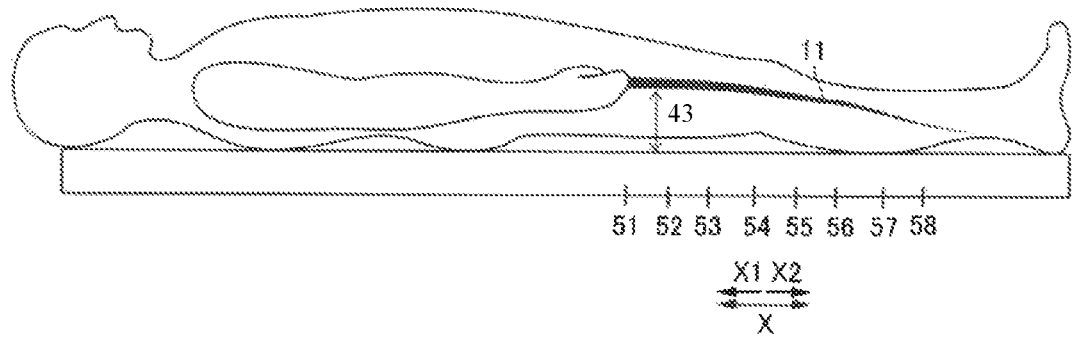

FIG. 10 is a diagram illustrating an example of a relation between a position coordinate and height information.

Figure 11:
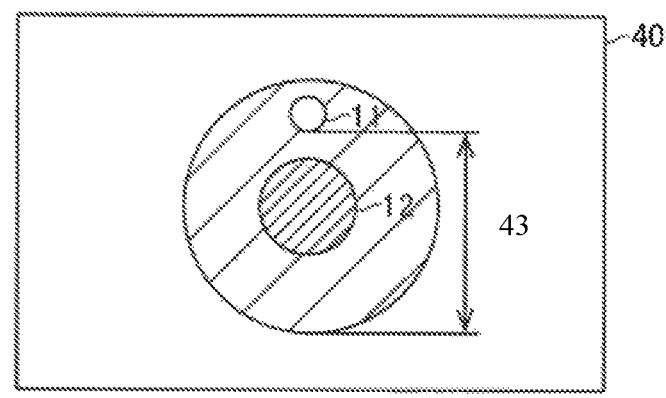

FIG. 11 is a diagram illustrating an example of a tomographic image.

Figure 12:
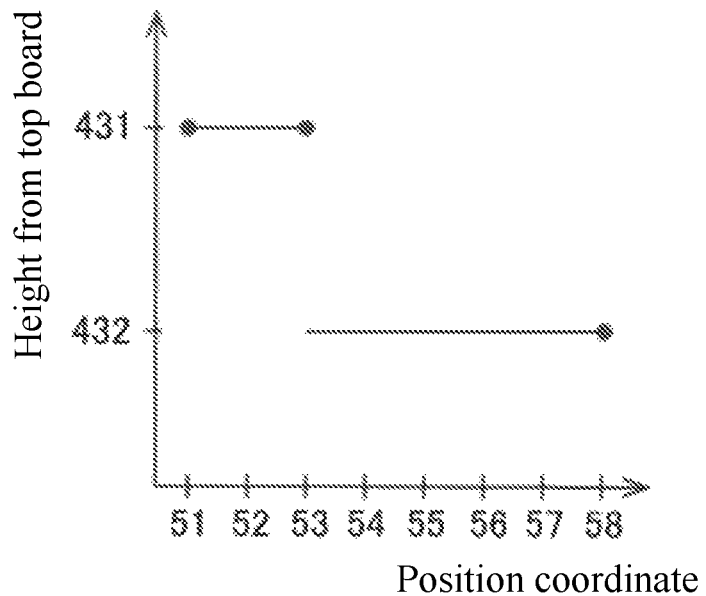

FIG. 12 is a diagram illustrating an example of a relation between a position coordinate and height information.

Figure 13:
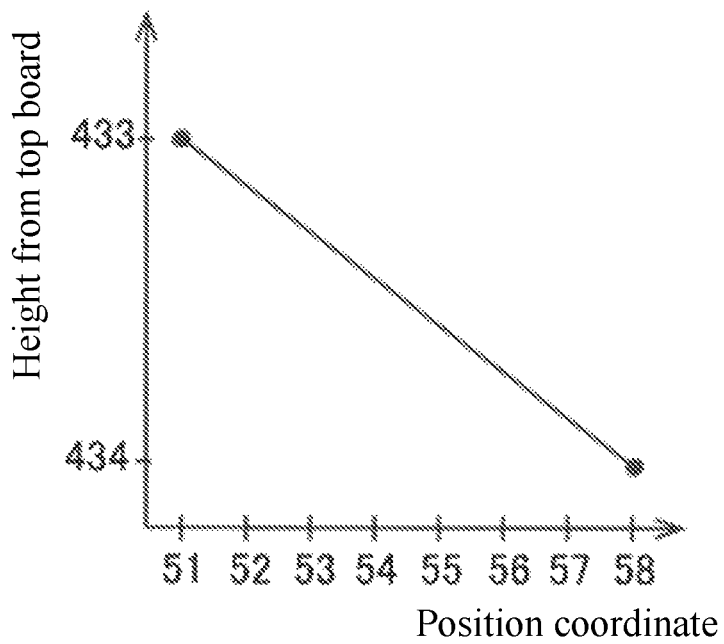

FIG. 13 is a diagram illustrating an example of a relation between a position coordinate and height information.

Figure 14:
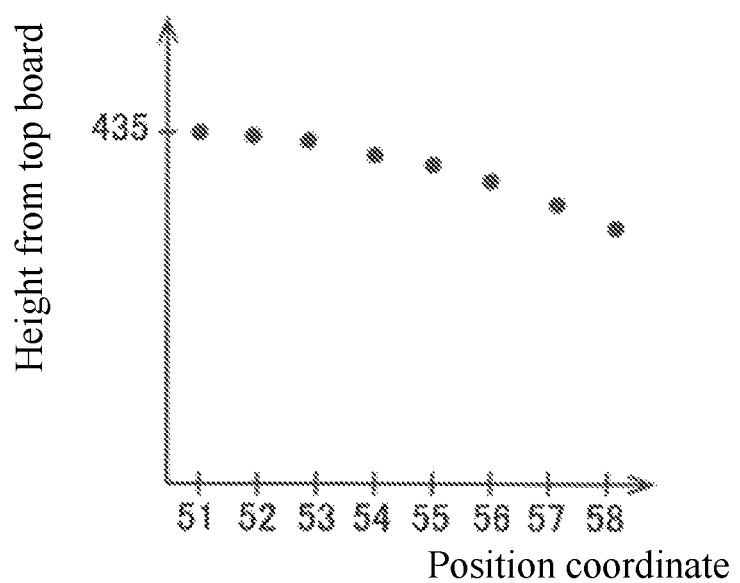

FIG. 14 is a diagram illustrating an example of a relation between a position coordinate and height information.

DESCRIPTION OF PREFERRED EMBODIMENTS

Hereinafter, embodiments in which the present invention is embodied will be described with reference to the attached drawings.

First Embodiment

With reference to FIG. 1 to FIG. 8, the configuration of the X-ray fluoroscopic imaging apparatus 100 according to this embodiment will be described.
(Configuration of X-Ray Fluoroscopic Imaging Apparatus)

Figure 1:
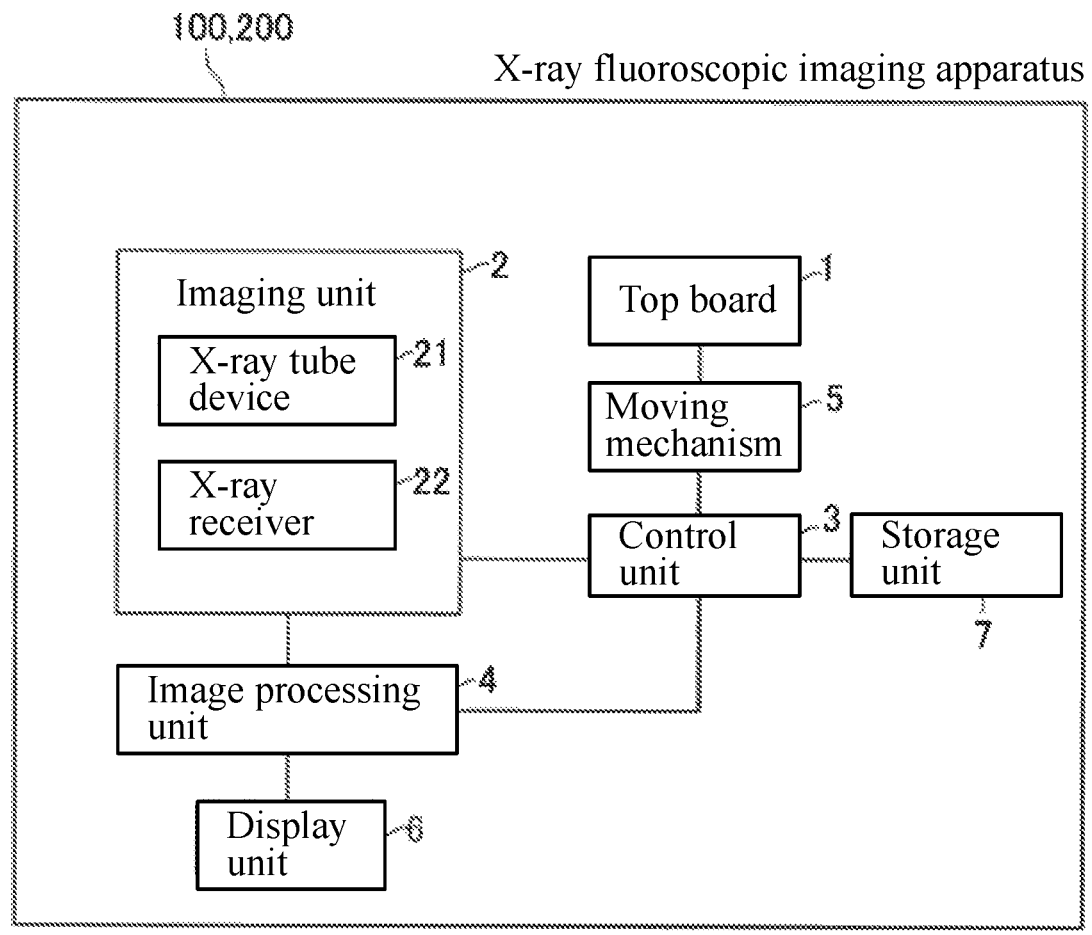
FIG. 1 is a block diagram showing a configuration of an X-ray fluoroscopic imaging apparatus.

As shown in FIG. 1, (a) of FIG. 2, and (b) of FIG. 2, the X-ray fluoroscopic imaging apparatus 100 of this embodiment is provided with a top board 1 for placing a subject 50 thereon, an imaging unit 2 including an X-ray tube device 21 and an X-ray receiver 22, a control unit 3, and an image processing unit 4. Note that the X-ray tube device 21 is an example of the "X-ray source" recited in claims. Also, note that the X-ray receiver 22 is an example of the "detection unit" recited in claims.

The top board 1 is formed in a rectangular flat plate shape in a plan view. The subject 50 is placed on the placing surface 1a of the top board 1 such that the head-foot direction of the subject 50 is along the direction along the long side of the rectangle and the left-right direction of the subject 50 is a direction along the short side of the rectangle. In this specification, note that it is assumed that the head-foot direction of the subject 50 is an X-direction, the left-right direction of the subject 50 is a Z-direction, and a direction perpendicular to the X-direction and the Z-direction is a Y-direction.

The X-ray tube device 21 is arranged on one side of the top board 1 in the Y-direction. The X-ray tube device 21 is configured to emit X-rays when a voltage is applied by an X-ray tube driver (not shown). The X-ray tube device 21 has a collimator capable of adjusting the X-ray irradiation field which is the irradiation area of X-rays. Further, as shown in (b) of FIG. 2, the X-ray tube device 21 is attached to the tip end of a C-shaped arm portion 23 on one side (Y2-side).

The X-ray receiver 22 is attached to the tip end of the other side (opposite side of the X-ray tube device 21) of the arm portion 23. That is, the X-ray receiver 22 is arranged on the other side of the top board 1 (the side opposite to the X-ray tube device 1) in the Y-direction across the top board 1. The X-ray receiver 22 is configured to detect X-rays and output detection signals. The X-ray receiver 22 includes, for example, an FPD (Flat Panel Detector). With this configuration, the X-ray fluoroscopic imaging apparatus 100 is configured so that the X-ray image 30 (see FIG. 11) can be captured by emitting X-rays in the Y-direction by the X-ray tube device 21 in a state in which the subject 50 is placed on the top board 1 and detecting the X-rays that have passed through the subject 50 by the X-ray receiver 22.

As shown in FIG. 1 and FIG. 3, the X-ray fluoroscopic imaging apparatus 100 is provided with a moving mechanism 5. The moving mechanism 5 is configured so that the top board 1 or the imaging unit 2 can be moved in any directions. That is, as shown in FIG. 3, by moving either one of or both of the top board 1 and the imaging unit 2 in either the X-direction, Y-direction or the Z-direction to change the relative position between the top board 1 and the imaging unit 2, the position (imaging position) at which the subject 50 is imaged can be changed. In this embodiment, the top board 1 is moved in the X-direction, and the imaging unit 2 is fixed.

As shown in FIG. 1, the control unit 3 is a computer including a CPU (Central Processing Unit), a ROM (Read Only Memory), a RAM (Random Access Memory), and the like.

As shown in FIG. 1, (a) of FIG. 2, and (b) of FIG. 2, the control unit 3 is configured to acquire the position information of the top board 1 and the imaging unit 2 moved by the moving mechanism 5. As the position information of the top board 1 and the imaging unit 2, a plurality of pieces of position coordinate information (X, Y, Z) is used. The position information of the imaging unit 2 includes the position information of the X-ray tube device 21 and the X-ray receiver 22. The position information of the imaging unit 2 uses, for example, the position coordinate information (X, Y, Z) at a total of four positions including any position of the X-ray tube device 21, any position of the X-ray receiver 22, and any two positions of the arm portion 23. The position information of the top board 1 uses the respective position coordinate information (X, Y, Z) at positions near the four corners of the top board 1.

The image processing unit 4 is a computer configured to include a processor such as a GPU (Graphics Processing Unit) or an FPGA (Field-Programmable Gate Array) configured to process images. The image processing unit 4 functions as an image processing apparatus by executing an image processing program. The image processing unit 4 is configured to generate an X-ray image 30 based on the detection signal output from the X-ray receiver 22.

The image processing unit 4 is configured to generate a first long image 31 based on first height information 41. The image processing unit 4 is configured to generate a second long image 32 upon acceptance of an input of second height information 42 after generating the first long image 31.

The display unit 6 is a display provided on the X-ray fluoroscopic imaging apparatus 100. On the display unit 6, in addition to the images generated by the image processing unit 4, a menu screen 61 for a user to input height information is displayed (see FIG. 7).

The storage unit 7 is a RAM included in the control unit 3. Images such as X-ray images 30 are stored in the storage unit 7.
(Long Image Capturing)

The generation of a long image in this embodiment will be described. In this embodiment, an example will be described in which a blood vessel 11 of a lower limb of a subject 50 is imaged. Note that the "blood vessel of a lower limb" is an example of the "imaging target portion" recited in claims.

When capturing an image of a blood vessel 11 of a lower limb, a user captures an X-ray image 30 while administering a contrast agent to the subject 50.

As shown in FIG. 3 and FIG. 4, the X-ray fluoroscopic imaging apparatus 100 is configured to generate a plurality of X-ray images 30 while changing the relative position between the top board 1 and the imaging unit 2 by moving the top board 1 with the moving mechanism 5. At this time, the X-ray fluoroscopic imaging apparatus 100 is configured to capture a predetermined number of X-ray images 30.

The X-ray receiver 22 is configured to detect the X-rays emitted from the X-ray tube device 21 and transmitted through the subject 50 and output a detection signal.

As shown in FIG. 4, the image processing unit 4 is configured to generate X-ray images 30 captured based on the detection signals of the X-ray receiver 22. The image processing unit 4 corrects the X-ray images 30 based on first height information 41 and generates a first long image 31 by stitching them together. When generating the first long image 31, a central portion of each X-ray image 30 may be extracted and the X-ray images are stitched together so that the extracted central portions are continuous with each other.

As shown in FIG. 5, the first height information 41 is set as a height of the top board 1 or a height from the placing surface 1a of the top board 1 (e.g., 10 cm from the top board). Alternatively, the first height information 41 is set, for example, at the position of an isocenter. The first height information 41 is one of the setting data of the X-ray fluoroscopic imaging apparatus 100 and is stored in the storage unit 7 as a default value.

As shown in FIG. 1 and FIG. 6, the control unit 3 is configured to perform control for displaying a generated image on the display unit 6. In FIG. 6, a first long image 31 is displayed on the display unit 6.

Confirming the first long image 31, the user determines whether or not the stitching accuracy of the first long images 31 is adequate. In some cases, however, there is a case in which the stitching accuracy of the generated first long image 31 are insufficient. In this case, the range for correcting the magnification and second height information 42 is determined. As the range for correcting the magnification of the first long image 31, the range of frames of the X-ray images 30 captured at positions where the magnification is desired to be changed among X-ray images is set. The frame indicates the order of capturing X-ray images 30. For example, it is assumed that the X-ray image 30 captured at the first time is an X-ray image 30 of one frame.

As shown in FIG. 7, when performing regeneration of a long image (generation of a second long image 32), the control unit 3 is configured to control the display unit 6 to display a menu screen 61 for correcting a height. The menu screen 61 is configured such that the range of the frame to be corrected and second height information 42 can be input.

The second height information 42 is determined based on, for example, the relative positional relationship between the blood vessel 11 and the X-ray tube device 21. The blood vessel 11 positioned closer to the X-ray tube device 21 is imaged in a large size in the X-ray image 30, and the blood vessel 11 positioned away from the X-ray tube device 21 is imaged in a small size in the X-ray image 30. Therefore, the user inputs second height information 42 so that the X-ray image becomes small when the blood vessel 11 in which the stitching of the first long image 31 is unnatural is positioned close to the X-ray tube device 21 and inputs second height information 42 so that the X-ray image becomes larger when the blood vessel 11 in which the stitching of the first long image 31 is unnatural is positioned away from the X-ray tube device 21.

Receiving an input of the preview button 62 by the user, the image processing unit 4 corrects the magnification of the X-ray image 30 in the frame of the input range based on the input second height information 42 and generates the second long image 32. As shown in FIG. 8, the control unit 3 is configured to control the display unit 6 to display a preview of the second long image 32 reconstructed from the corrected X-ray images 30.

The user can check the displayed second long image 32 and enter height information again if the image is not the desired image. When it becomes a desired second long image 32, the generation button 63 is pressed, so that the second long image 32 is stored in the storage unit 7.

(Operation of X-Ray Fluoroscopic Imaging Apparatus in Generating Long Image)

Next, referring to FIG. 9, the operation of the X-ray fluoroscopic imaging apparatus 100 for generating a long image according to this embodiment will be described.

In Step 90, the X-ray fluoroscopic imaging apparatus 100 begins capturing X-ray images 30.

In Step 91, the image processing unit 4 corrects the magnification of the X-ray image 30 based on the first height information 41 and then generates a first long image 31 by stitching together the acquired X-ray images 30 based on the position coordinate. Note that the image processing unit 4 does not use images containing exactly the same position coordinate.

In Step 92, the control unit 3 is configured to perform control for displaying the generated first long image 31 on the display unit 6.

In Step 93, the following Step differs depending on whether or not there is a re-generation input from the user. When the user performs a re-generation input, the process proceeds to Step 94, and when not, the process proceeds to Step 99.

In Step 94, the X-ray fluoroscopic imaging apparatus 100 accepts an input of the range of frames of X-ray images 30 to be corrected. Further, in Step 95, the X-ray fluoroscopic imaging apparatus 100 accepts an input of second height information 42. The order of performing Step 94 and Step 95 may be reversed.

In Step 96, the image processing unit 4 corrects the magnification of the X-ray images 30 of in the rage of frames input in Step 94 based on the second height information 42 input in Step 95. In Step 97, the control unit 3 controls the display unit 6 to display the reproduced second long image 32 based on the user's input of the preview button 62.

In Step 98, when an input for generating an image is accepted from the user, the process proceeds to Step 99, and the image processing unit 4 generates a second long image 32 and stores it in the storage unit 7. In Step 98, when there is no input for generating an image by the user, the process returns to Step 95 to accept the input of second height information 42 from the user.

Effects of This Embodiment

According to this embodiment, the following effects can be obtained.

In this embodiment, the X-ray fluoroscopic imaging apparatus is provided with: the top board 1 configured to place a subject 50 thereon; the imaging unit 2 including the X-ray tube device 21 configured to emit X-rays to the blood vessel 11 in the subject 50 placed on the top board 1 and the X-ray receiver 22 configured to detect X-rays emitted from the X-ray tube device 21 and transmitted through the subject 50 and configured to capture a plurality of X-ray images of the subject 50 while changing the relative position with respect to the top board 1; and the image processing unit 4 configured to generate a first long image 31 by correcting the magnification of the plurality of X-ray images 30 based on first height information 41 and stitching them together, wherein the image processing unit 4 is configured to generate a second long image 32 in which the magnification of the plurality of X-ray image is corrected based on second height information upon acceptance of an input on the second height information 42 after generating the first long image 31. With this, after generating the first long image 31 using the first height information 41, by changing the magnification of the X-ray image 30 by the second height information 42, the size of the X-ray image 30 can be adjusted. Therefore, it is possible to generate a long image with high stitching accuracy.

In this embodiment, the image processing unit 4 is configured to accept a selection of one or more of the plurality of X-ray images 30 and generate a partial second long image 32 using the one or more of the plurality of X-ray image 30 selected from the plurality of X-ray images 30. With this, the user can generate a second long image 32 in which only a desired part of the blood vessel 11 of the lower limb is enlarged or reduced. Further, the processing rate of the image processing unit 4 increases as compared with the case of regenerating the entire second long image.

In this embodiment, the image processing unit 4 is configured to accept a selection of one or more of X-ray images 30 to be used for generating a second long image 32 upon acceptance of an input of the range of frames in which the magnification is corrected by the second height information 42 among frames, which are the order of capturing the plurality of X-ray images 30. With this, since the X-ray images 30 in the range of the input frames are corrected using the same second height information 42, the corrected X-ray images 30 become the same in size, so that the stitching accuracy can be improved.

In this embodiment, the image processing unit 4 is configured to generate a partial second long image 32 covering from the start frame to the end frame upon acceptance of an input of the start frame and the end frame for generating the second long image 32. This makes it possible to finely perform setting for generating the second long image 32 within the desired range.

In the embodiment, the X-ray fluoroscopic imaging apparatus 100 is further provided with the display unit 6, and the image processing unit 4 is configured to display a first long image 31 on the display unit 6, and then make the display unit 6 preview the generated second long image and enable to accept a re-input of the second height information 42. With this, the generated second long image 32 is previewed, so that the user can confirm whether or not the desired second long image 32 has been generated. Also, since it is configured such that the second height information 42 can be re-input, after the preview is displayed, the user can correct the magnification of the displayed second long image 32 to generate a desired second long image 32.

In this embodiment, the X-ray fluoroscopic imaging apparatus 100 is further provided with the storage unit 7 for storing images, and the image processing unit 4 is configured to store the second long image 32 generated immediately before acceptance of an operation input in the storage unit 7 upon acceptance of the operation input for completing the generation process of the second long image 32. With this configuration, the second long image 32 desired by the user can be stored and can be used to, e.g., acquire the second height information 42 when another second long image 32 is generated.

MODIFIED EXAMPLES

It should be noted that the embodiment disclosed herein is to be considered in all respects as illustrative and not restrictive. The scope of the present invention is indicated by claims rather than by the aforementioned description of the embodiment, and the scope of the present invention includes all modifications (changes) within the meaning and scope equivalent to claims.

First Modified Example

In a first modified example, the X-ray fluoroscopic imaging apparatus 100 is configured such that the control unit 3 performs control for acquiring the height information 43 (third height information) from tomographic images 40 of a blood vessel 11 or images of a blood vessel 11 captured at different angles. When acquiring X-ray images 30 for generating a long image, the subject 50 is irradiated with X-rays in the Y-direction. The images captured at different angles denote X-ray images 30 captured by emitting X-rays in a direction different from the Y-direction such as the Z-direction. The same reference numerals are used to denote the same portions as in this embodiment, and descriptions thereof will be omitted.

As shown in FIG. 1 and FIG. 10, the control unit 3 is configured to perform control for acquiring the height information 43 of the blood vessel 11 whose height from the top board 1 differs depending on the relative position between the blood vessel 11 and the top board 1 (i.e., the relative position from the position coordinate 51 to the position coordinate 58). In the case of a blood vessel 11 of a lower limb, the control unit 3 may be configured to perform control for acquiring the height information 43 for each region, such as the height information 43 of the blood vessel above the knee (from the position coordinate 51 to the position coordinate 53) and the height information 43 of the blood vessel below the knee (from the position coordinate 54 to the position coordinate 58), or may be acquired by subdividing the region. Further, the control unit 3 may be configured to acquire the height information 43 between the image capturing starting position (position coordinate 51) and the image capturing ending position (position coordinate 58). The control unit 3 may also be configured to perform control for acquiring a plurality of pieces of height information 43 in the blood vessel 11 of the lower limb.

The control unit 3 is configured to perform control for acquiring the position coordinate on the relative position between the top board 1 and a blood vessel 11. Further, the control unit 3 is configured to perform control for acquiring the height information 43 in association with the position coordinate of the blood vessel 11.

As shown in FIG. 11, the tomographic image 40 is, for example, an image captured using a CT (computed tomography) or an image captured using an Mill (magnetic resonance imaging), but is not limited thereto as long as the image is an image in which height information of the imaging target region from the top board 1 is obtained. In FIG. 11, the tomographic image 40 of the lower limb is shown in a simplified manner, and the bone 12 and the blood vessel 11 which is an imaging target portion are imaged. The image obtained by imaging the blood vessel 11 at different angles is, for example, an image obtained by imaging the subject 50 from the side (Z1-direction). The height information 43 is obtained by specifying the blood vessel 11 from the tomographic image 40 or the image, and the height information of the blood vessel 11 is acquired from the position coordinate of the specified blood vessel 11.

As shown in FIG. 12 to FIG. 14, the image processing unit 4 is configured to correct the magnification of the plurality of X-ray images 30 based on the position coordinate of the blood vessel 11 and the plurality of pieces of height information 43. In FIG. 12 to FIG. 14, the horizontal axis represents the position coordinate, and the vertical axis represents the height (height information) from the top board 1 to the blood vessel 11. The position coordinate corresponds to the position coordinate of FIG. 10. Although the example illustrates eight position coordinates, the number of position coordinates is not limited to eight.

With reference to FIG. 12, the case in which the range of the position coordinate and the height information 43 are acquired in association with each other will be described. In cases where the range of the position coordinate from the position coordinate 51 to the position coordinate 53 and the height information 431 are associated, it is configured to make corrections based on the range of the position coordinates from the position coordinate 51 to the position coordinate 53 and the height information 431. More specifically, the X-ray image 30 in which the position coordinate 52 is the center position coordinate is corrected so that the blood vessel 11 of the position coordinate 51 in which the position coordinate 51 is the center position coordinate becomes the same size as that of the portion to be stitched thereto. Similarly, it is configured to correct the X-ray image 30 in which the position coordinate 53 is the center coordinate of the X-ray image 30. Also, in cases where the range of the position coordinate from the position coordinate 54 to the position coordinate 58 and the height information 432 are associated, the image processing unit 4 is configured such that the X-ray image 30 at the position coordinate 54, the X-ray image 30 at the position coordinate 55, the X-ray image 30 at the position coordinate 56, and the X-ray image 30 at the position coordinate 57 are corrected based on the height information 432.

Specifically, the control unit 3 is configured to correct the X-ray images 30 based on the height information 431 so that the blood vessel 11 of the X-ray image 30 in which the position coordinate 54 is the center position coordinate and the X-ray image 30 in which the position coordinate 53 is the center coordinate are stitched to each other in a smoothly connected manner. Similarly, the image processing unit 4 is configured to correct the X-ray images 30 in which the position coordinates from the position coordinate 55 to the position coordinate 58 are the center coordinates.

With reference to FIG. 13, the case in which the height information 433 at the image capturing starting position and the height information 434 at the image capturing ending position are acquired will be described. When the height information 433 at the position coordinate 51 which is the image capturing starting position and the height information 434 at the position coordinate 58 which is the image capturing ending position are acquired, the control unit 3 is configured to acquire the distribution of the height information 43 by a line connecting the height information 433 at the position coordinate 51 which is the image capturing starting position and the height information 434 at the position coordinate 58 which is the image capturing ending position. The control unit 3 is configured to control the image processing unit 4 so that the X-ray image 30 in which the position coordinate 51 is the center position coordinate is corrected in size based on the height information 433 and the X-ray image 30 in which the position coordinate 58 is the center position coordinate 58 is corrected in size based on the height information 434. With respect to the X-ray images 30 including the position coordinate 52 to the position coordinate 57 as the respective center position coordinates, the control unit 3 is configured to control the image processing unit 4 to acquire the height information 43 from the graphs, correct the size based on the acquired height information 43, and increase or reduce the size.

With reference to FIG. 14, the case in which the height information 43 is acquired for each position coordinate will be described. For example, when the height information 435 at the position coordinate 51 is input, the magnification of the X-ray image 30 having the position coordinate 51 as a center coordinate is corrected based on the height information 435. Similarly, the X-ray image 30 having the position coordinate 52 as a center coordinate is enlarged or reduced based on the height information 43 input as the height information of the position coordinate 52 to be smoothly stitched to the X-ray image 30 having the position coordinate 51 as a center coordinate.

Effects of First Modified Example

In this embodiment, as described above, the X-ray fluoroscopic imaging apparatus 200 includes the top board 1 configured to place a subject 50 thereon, the imaging unit 2 including the X-ray tube device 21 configured to irradiate the blood vessel 11 in the subject 50 placed on the top board 1 with X-rays and the X-ray receiver 22 configured to detect X-rays emitted from the X-ray tube device 21 and transmitted through the subject 50 and configured to capture a plurality of X-ray images 30 of the subject 50 while changing the relative position with respect to the top board 1, the control unit 3 configured to perform control for acquiring the plurality of pieces of height information 43 regarding the height of the blood vessel 11 from the top board 1 corresponding to the plurality of positions in a surface of the top board 1, and the image processing unit 4 configured to correct the magnification of the X-ray image 30 based on the plurality of positions in the surface of the top board 1 and the corresponding plurality of pieces of height information 43 and generate a long image by stitching together the plurality of X-ray images 30 in which the magnification has been corrected. As a result, the image processing unit 4 corrects the magnification of the X-ray images 30 based on the plurality of pieces of height information 43 acquired by the control unit 3, so that the size of the blood vessel 11 of the X-ray image 30 can be adjusted for each region. For this reason, by adjusting the size of the blood vessel 11 of the X-ray image 30, it is possible to generate a long image having the same size as that of the blood vessel 11 among the plurality of X-ray images 30 in the portion to be stitched with high connection accuracy.

Second Modified Example

In this embodiment, an example is described in which the image processing unit generates a long image, but in the second modified example, an example will be explained in which the image processing unit generates a differential long image. The rest of the configuration is the same as that of this embodiment, and the same reference numerals are allotted and descriptions thereof will be omitted.

The differential long image is an image generated by subtracting a non-contrast agent long image obtained by stitching together X-ray images captured in a state in which the contrast agent has not been administered to the subject from a contrast agent long image obtained by stitching together X-ray images captured in a state in which the contrast agent has been administered to the subject.

In the second modification, the long image and the differential long image are corrected based on the second height information. Correcting the first long image and the differential long image using the second height information is performed in the same manner as in this embodiment.

In the second modified example, even in cases where artifacts occur in the differential long image 34 due to the body movements of the subject at the time of diagnostic, there is an advantage that the contrast agent long image can be used.

Other Modified Example

For example, in the above embodiment, the X-ray fluoroscopy is performed by moving the top board in the X-direction and the Y-direction with respect to the imaging unit, but the present invention is not limited thereto. In this embodiment, the top board moving imaging may be performed by moving the imaging unit in the X-direction and the Y-direction with respect to the top board. Alternatively, the top board 1 and the imaging unit may be moved only either in the X-direction or in the Y-direction. Also, the top board moving imaging may be performed by moving either the top board or the imaging unit in the X-direction or the Y-direction while moving in the Z-direction.

In the above embodiment, an example is shown in which the lower limb portion of the subject is radiographed, but the present invention is not limited to this. In this embodiment, a portion other than a lower limb portion, such as an arm portion and a torso portion of a subject, may be radiographed. Further, in the present invention, the subject is not limited to a human body, and an X-ray fluoroscopic imaging apparatus for imaging a subject which is an animal other than a human body may be configured.

In the above embodiment, an example is shown in which the imaging target portion is a blood vessel, but the present invention is not limited to this. In the present invention, the imaging target portion may be an internal organ other than a blood vessel.

In the first modification described above, an example is shown in which the range of the position coordinate and the height information are associated with each other, but the present invention is not limited to this. For example, the number of X-ray images and the height information may be associated with each other.

In the first modification, an example is shown in which images captured from the side of the subject are used as images captured at different angles, but the present invention is not limited to this. The images may be images captured from oblique orientations of the subject as long as the images are capable of acquiring the height information.

[Aspects]

It will be understood by those skilled in the art that the above described exemplary embodiments are concrete examples of the following aspects.

(Item 1)

An X-ray fluoroscopic imaging apparatus comprising:
a top board configured to place a subject thereon;
an imaging unit including an X-ray source configured to emit X-rays to an imaging target portion in the subject placed on the top board and a detection unit configured to detect X-rays emitted from the X-ray source and transmitted through the subject, the imaging unit being configured to capture a plurality of X-ray images of the subject while changing a relative position with respect to the top board; and
an image processing unit configured to generate a first long image by correcting a magnification of the plurality of X-ray images based on first height information and stitching them together,
wherein the image processing unit is configured to generate a second long image in which the magnification of the plurality of X-ray images is corrected based on second height information upon acceptance of an input of the second height information after generating the first long image.

(Item 2)

The X-ray fluoroscopic imaging apparatus as recited in the aforementioned Item 1,
wherein the image processing unit is configured to accept a selection of one or more of the plurality of X-ray images and generate a part of the second long image using the one or more of the plurality of X-ray images selected from the plurality of X-ray images.

(Item 3)

The X-ray fluoroscopic imaging apparatus as recited in the aforementioned Item 2,
wherein the image processing unit is configured to accept a selection of an X-ray image to be used for generating the second long image upon acceptance of an input of a range of frames in which the magnification is to be corrected by the second height information among the frames arranged in order of capturing the plurality of X-ray images.

(Item 4)

The X-ray fluoroscopic imaging apparatus as recited in the aforementioned Item 3,
wherein the image processing unit is configured to generate a part of the second long image composed of from a start frame to an end frame upon acceptance of an input of the start frame and the end frame for generating the second long image.

(Item 5)

The X-ray fluoroscopic imaging apparatus as recited in the aforementioned Item 1,
further comprising a display unit,
wherein the image processing unit is configured to make the display unit preview the first long image and enable to accept a re-input of the second height information when the second long image is generated upon acceptance an input of the second height information after making the display unit display the first long image.

(Item 6)

The X-ray fluoroscopic imaging apparatus as recited in the aforementioned Item 4,
further comprising a storage unit for storing images,
wherein the image processing unit is configured to store the second long image generated immediately before receiving an operation input for completing generation processing of the second long image in the storage unit when the operation input is accepted.

(Item 7)

An X-ray fluoroscopic imaging apparatus comprising:
a top board configured to place a subject thereon;
an imaging unit including an X-ray source configured to emit X-rays to an imaging target portion in the subject placed on the top board and a detection unit configured to detect X-rays emitted from the X-ray source and transmitted through the subject, the imaging unit being configured to capture a plurality of X-ray images of the subject while changing a relative position with respect to the top board;
a control unit configured to perform control for acquiring a plurality of pieces of height information on a height of the imaging target portion from the top board corresponding to a plurality of positions in a plane of the top board; and
an image processing unit configured to correct a magnification of the plurality of X-ray images based on the plurality of positions in the plane of the top board and corresponding plurality of pieces of height information and generate a long image by stitching together the plurality of X-ray images in which the magnification has been corrected.

The invention claimed is:

1. An X-ray fluoroscopic imaging apparatus comprising:
a top board configured to place a subject thereon;
an imaging unit including an X-ray source configured to emit X-rays to an imaging target portion in the subject placed on the top board and a detection unit configured to detect X-rays emitted from the X-ray source and transmitted through the subject, the imaging unit being configured to capture a plurality of X-ray images of the subject while changing a relative position with respect to the top board; and
an image processing unit configured to generate a first long image by correcting a magnification of the plurality of X-ray images based on first height information and stitching them together,
wherein the image processing unit is configured to generate a second long image in which the magnification of one or more of the plurality of X-ray images is corrected based on second height information upon acceptance of an input of the second height information after generating the first long image.

2. The X-ray fluoroscopic imaging apparatus as recited in claim 1,
wherein the image processing unit is configured to accept a selection of one or more of the plurality of X-ray images and generate a part of the second long image using the one or more of the plurality of X-ray images selected from the plurality of X-ray images.

3. The X-ray fluoroscopic imaging apparatus as recited in claim 2,
wherein the image processing unit is configured to accept a selection of an X-ray image to be used for generating the second long image upon acceptance of an input of a range of frames in which the magnification is to be corrected by the second height information among the frames arranged in order of capturing the plurality of X-ray images.

4. The X-ray fluoroscopic imaging apparatus as recited in claim 3,
wherein the image processing unit is configured to generate a part of the second long image composed of from a start frame to an end frame upon acceptance of an input of the start frame and the end frame for generating the second long image.

5. The X-ray fluoroscopic imaging apparatus as recited in claim 1,
further comprising a display unit,
wherein the image processing unit is configured to make the display unit preview the first long image and enable to accept a re-input of the second height information when the second long image is generated upon acceptance an input of the second height information after making the display unit display the first long image.

6. The X-ray fluoroscopic imaging apparatus as recited in claim 4,
further comprising a storage unit for storing images,
wherein the image processing unit is configured to store the second long image generated immediately before accepting an operation input for completing generation processing of the second long image in the storage unit when the operation input is accepted.

7. An X-ray fluoroscopic imaging apparatus comprising:
a top board configured to place a subject thereon;
an imaging unit including an X-ray source configured to emit X-rays to an imaging target portion in the subject placed on the top board and a detection unit configured to detect X-rays emitted from the X-ray source and transmitted through the subject, the imaging unit being configured to capture a plurality of X-ray images of the subject while changing a relative position with respect to the top board;
a control unit configured to perform control for acquiring a plurality of pieces of height information on a height of the imaging target portion from the top board corresponding to a plurality of positions in a plane of the top board; and
an image processing unit configured to correct a magnification of the plurality of X-ray images based on the plurality of positions in the plane of the top board and corresponding plurality of pieces of height information and generate a long image by stitching together the plurality of X-ray images in which the magnification has been corrected.

* * * * *